(12) United States Patent
Brunner et al.

(10) Patent No.: US 12,042,563 B2
(45) Date of Patent: Jul. 23, 2024

(54) COMPRESSED TABLETS

(71) Applicant: DSM IP ASSETS B.V., Heerlen (NL)

(72) Inventors: Dominik Brunner, Kaiseraugst (CH); Laure Clasadonte, Kaiseraugst (CH); Emmanuel Heinrich, Kaiseraugst (CH); Roland Schuepfer, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/628,414

(22) PCT Filed: Jun. 25, 2018

(86) PCT No.: PCT/EP2018/066957
§ 371 (c)(1),
(2) Date: Jan. 3, 2020

(87) PCT Pub. No.: WO2019/007740
PCT Pub. Date: Jan. 10, 2019

(65) Prior Publication Data
US 2020/0155462 A1 May 21, 2020

(30) Foreign Application Priority Data
Jul. 7, 2017 (EP) ..................................... 17180187

(51) Int. Cl.
*A61K 9/20* (2006.01)
*A61K 9/28* (2006.01)
*A61K 31/04* (2006.01)

(52) U.S. Cl.
CPC .......... *A61K 9/2063* (2013.01); *A61K 9/2009* (2013.01); *A61K 9/2031* (2013.01); *A61K 9/2095* (2013.01); *A61K 9/288* (2013.01); *A61K 31/04* (2013.01)

(58) Field of Classification Search
CPC .. A61K 9/2063; A61K 9/2009; A61K 9/2031; A61K 9/2095; A61K 9/288; A61K 31/04
See application file for complete search history.

(56) References Cited

U.S. PATENT DOCUMENTS

| 3,089,825 A | 5/1963 | Brenner | |
|---|---|---|---|
| 3,925,343 A * | 12/1975 | Hampton | A23J 3/18 530/374 |
| 2006/0127480 A1* | 6/2006 | Tobyn | A61K 9/143 424/484 |
| 2009/0011019 A1* | 1/2009 | Jahagirdar | A61K 9/0095 424/472 |
| 2015/0376113 A1* | 12/2015 | Duval | A23K 50/10 514/355 |

FOREIGN PATENT DOCUMENTS

| CN | 1863515 | 11/2006 | |
|---|---|---|---|
| CN | 1863516 | 11/2006 | |
| WO | 2012/084629 | 6/2012 | |
| WO | WO-2017137489 A1 * | 8/2017 | ......... A61K 31/4406 |

OTHER PUBLICATIONS

Machine Translation of CN 103598595, Jia et al., 2014, Patentscope. (Year: 2014).*
Haisan, J et al., The effects of feeding 3-nitrooxypropanol on methane emissions and productivity of Holstein cows in mid lactation, 2014, Journal of Dairy Science, 97, 3110-3119 (Year: 2014).*
Li et al; "Study on montmorillonite/gluten in sustained-release system," Applied Chemical Industry, vol. 40, No. 6, 2011.
International Search Report for PCT/EP2018/066957 dated Oct. 15, 2018, 3 pages.
Written Opinion of the ISA for PCT/EP2018/066957 dated Oct. 15, 2018, 5 pages.

* cited by examiner

*Primary Examiner* — David J Blanchard
*Assistant Examiner* — Ayaan A Alam
(74) *Attorney, Agent, or Firm* — NIXON & VANDERHYE P.C.

(57) ABSTRACT

The present invention relates to compressed tablets comprising 3-nitrooxypropanol or derivatives thereof and a gluten as well as to the production of such tablets.

11 Claims, 1 Drawing Sheet

COMPRESSED TABLETS

CROSS-REFERENCE TO RELATED APPLICATIONS

This application is the U.S. national phase of International Application No. PCT/EP2018/066957 filed Jun. 25, 2018 which designated the U.S. and claims priority to EP Application No. 17180187.1 filed Jul. 7, 2017, the entire contents of each of which are hereby incorporated by reference.

FIELD

The present invention relates to compressed tablets comprising 3-nitrooxypropanol or derivatives thereof and a gluten as well as to the production of such tablets.

BACKGROUND AND SUMMARY

The temperature of the air surrounding the earth is increasing, a process referred to as global warming. One of the main focuses to reduce this warming effect is to reduce the amount of greenhouse gases emitted into the atmosphere. Greenhouse gases are emitted from several different sources, both natural and artificial; however, the two sources with the most emphasis are the agricultural and fossil fuel industries. Within agriculture, ruminants and in particular cattle are the major contributors to the biogenic methane formation, and it has been estimated that the prevention of methane formation from ruminants would almost stabilize atmospheric methane concentrations.

Methane production in ruminants is due to the presence of methanogenic archaea in the rumen, which however need energy, nitrogen and minerals to grow. Thus, the number of methanogenic archaea in the rumen and concomitantly the methane emission generally slowly increases after feeding.

3-Nitrooxypropanol and structural analogues thereof have been reported to inhibit the growth of methanogenic archaea and thus significantly reducing the methane production in ruminants (WO2012/084629). So far, 3-nitrooxypropanol is supplemented to ruminants as 10% 3-nitrooxypropanol on silicon dioxide, a product form which instantly releases the active into the aqueous rumen fluid. As the increase in the number of methanogenic archaea is however slowly evolving after feeding, an instant release of the active is not particularly suitable to achieve long term methane reduction.

Thus, there is an ongoing need to develop a product form comprising 3-nitrooxypropanol or derivatives thereof, which shows no or only slow disintegration and a slow-release of the active in aqueous media over an extended period of time, such as 2-24 hours, e.g. 4 to 8 hours.

Surprisingly, it has been found that compressed (compacted) tablets comprising 3-nitrooxypropanol and a gluten remain intact and show no disintegration over a long period of time and only slowly release the active into aqueous media and are thus suitable to overcome the above-mentioned problems.

Thus, in a first embodiment the present invention relates to compressed tablets (I) comprising
(i) at least 0.01 wt-%, based on the total weight of the compressed tablet, of a compound of formula (I)

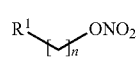

formula (I)

wherein
n is an integer from 1 to 46
$R^1$ is H, $C_1$-$C_6$alkyl, phenyl, —OH, —NH$_2$, —CN, —COOH, —O(C=O)$R^8$, —NHC(=O)$R^8$, SO$_2$NH$R^8$, or —ONO$_2$, and
$R^8$ is $C_1$-$C_6$alkyl, phenyl, pyridyl such as preferably 2-pyridyl with the proviso that when n is >3 the hydrocarbon chain may be interrupted by —O— or —NH—, and
(ii) at least 30 wt-%, based on the total weight of the compressed tablet, of a gluten.

The at least one compound of formula (I) can be incorporated into the tablet as such or absorbed on carrier. In a preferred embodiment, the compound of formula (I) is incorporated into the tablet absorbed on a carrier.

Thus, in a second embodiment, the present invention relates to compressed tablets (II) with all the preferences and definitions as given herein wherein the compound of formula (I) is absorbed on a carrier.

Particular advantageous compounds of formula (I) in all embodiments of the present invention are compounds of formula (II) wherein n is an integer between 3 and 9 and $R^1$ is OH, COOH or —ONO$_2$.

Even more advantageous compounds of formula (I) are 3-nitrooxypropanol (CAS-No: 100502-66-7), 9-nitrooxynonanol, 5-nitroxy pentanoic acid (CAS 74754-56-6), 6-nitroxy hexanoic acid (CAS 74754-55-5), Bis(2-hydroxyethyl)amine dinitrate (CAS 20830-49-3), 1,4-bis-nitrooxybutane (CAS 3457-91-8) and 1,5-bis-nitrooxypentane (CAS 3457-92-9). Most preferred in all embodiments of the present invention is 3-nitrooxypropanol.

The compounds according to the present invention are known and either commercially available or can be prepared in analogy to the processes as e.g. disclosed in WO2012/084629.

DETAILED DESCRIPTION

Figures 1, 2, 3, 4:
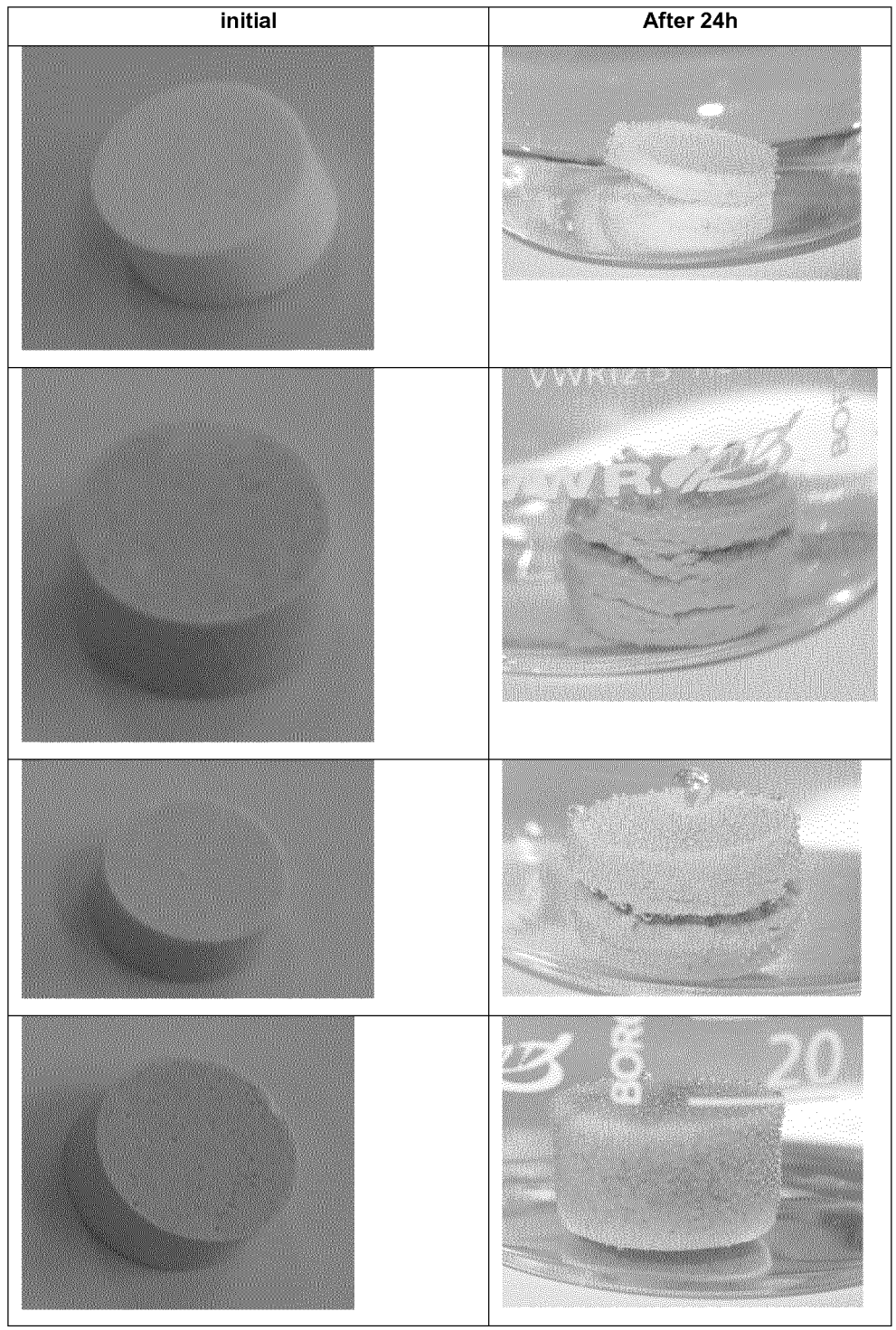
FIGS. 1-4 are photographs showing the respective tablet disintegration test results conducted according to the Example 1c below for tablets R2, R3, R4 and I1 after initial immersion in 100 mL tap water and after 24 hours immersion.

The amount of the compound of formula (I) in the tablets according to the present invention is preferably selected in the range of 0.01 to 10 wt.-%, more preferably in the range of 0.05 to 5 wt.-%, most preferably in the range of 0.075 to 2.5 wt.-%, based on the total weight of the tablet.

Gluten is the protein found in many grains and cereals such as wheat, corn, oats, rye and barley. The term "gluten" as used herein refers to gluten from any available source and to mixtures of gluten from various sources. Preferably, in all embodiments of the present invention wheat gluten, more preferably vital wheat gluten (CAS 93384-22-6) is used. Such vital wheat gluten having a protein content of at least 83% is e.g. obtainable as Viten® (wheat gluten supra vital) at Roquette or GluVital™ at Cargill.

The amount of gluten in the tablets according to the present invention is preferably at least 40 wt.-%, more preferably at least 50 wt.-%, even more preferably at least 60 wt.-%, and most preferably at least 70 wt.-%, based on the total weight of the tablet.

The term carrier as used herein refers to any carrier material suitable to absorb active ingredient to be supplemented to animals (including humans). Particular suitable carriers according to the present invention encompass silicon dioxide, maltodextrin, limestone, cyclodextrin, wheat as well as mixtures thereof.

The tablets according to the present invention are compressed powders, which depending on the process of production as well as the storage conditions, may comprise some water. Generally, the moisture content of the tablets according to the present invention is below 12 wt.-%. Therefore, a further embodiment of the present invention relates to tablets according to the present invention having a moisture content of maximum 12 wt.-%, preferably maximum of 10 wt.-%, more preferably maximum 8 wt.-%, most preferably maximum of 6 wt.-%, based on the total weight of the tablets.

The tablets according to the present invention may furthermore contain additional (active) ingredients, excipients, and/or auxiliary agents (in the following referred to as additives) suitable to produce compressed tablets and for feed application. Such additives are well known to a person skilled in the art. The amount of these additives in the tablets according to the present invention can vary and depends on the compressed tablets to be produced.

Advantageously, the (total) amount of additive(s) present in the tablets according to the present invention is selected in the range of 0.1 to 40 wt.-%, preferably in the range of 0.1 to 30 wt.-%, more preferably in the range of 0.1 to 20 wt.-% based on the total weight of the tablet.

Thus, in a particular advantageous embodiment, the present invention relates to compressed tablets (Ill) with all the preferences and definitions as given herein, consisting essentially of
(i) 0.01 to 10 wt-%, preferably 0.05 to 5 wt.-%, more preferably 0.075 to 2.5 wt.-%, based on the total weight of the compressed tablet, of a compound of formula (I), optionally absorbed on a carrier, and
(ii) at least 50 wt.-%, preferably at least 60 wt.-%, more preferably at least 70 wt.-%, based on the total weight of the formulation, of gluten, and
(iii) 0.1 to 40 wt-%, preferably 0.1 to 30 wt.-%, more preferably 0.1 to 20 wt.-%, based on the total weight of the compressed tablet, of at least one additive, and
(iv) 0 to 10 wt-%, more preferably 0 to 8 wt.-%, most preferably 0 to 6 wt.-%, based on the total weight of the compressed tablet, of water.

The term 'consisting essentially of' as used in the context of the invention means that the addition of the wt-% of the ingredients (i) to (iv) add up to 100 wt.-%. However, it cannot be excluded that small amounts of impurities may be present such as e.g. in amounts of less than 5 wt.-%, preferably less than 3 wt.-% which are introduced via the respective raw materials or processes used.

Particularly suitable additives to be used in the tablets according to the present invention encompass fillers, lubricants, proteins, dyes, flavours, sweeteners, minerals, vitamins, and antioxidants without being limited thereto.

Particularly suitable fillers according to the present invention encompass mono-, di- and tri-calcium phosphate, limestone (calcium carbonate), magnesium carbonate, silicate compounds (magnesium and aluminum silicate), magnesiumoxide, microcrystalline cellulose, proteins, silicon dioxide as well as mixtures thereof, such as more in particular microcrystalline wax, microcrystalline cellulose and limestone as well as mixtures thereof, most preferably microcrystalline cellulose.

If present, the total amount of filler(s) in the tablets according to the present invention is advantageously selected in the range of 0 to 30 wt.-%, preferably in the range of 0 to 20 wt.-%, more preferably in the range of 0 to 15 wt.-% based on the total weight of the compressed tablet.

Particularly suitable lubricants according to the present invention are water insoluble lubricants and encompass magnesium stearate, calcium stearate, zinc stearate or stearic acid such as more in particular magnesium stearate and/or calcium stearate.

If present, the total amount of lubricant(s) in the tablets according to the present invention is advantageously selected in the range of 0.1 to 5 wt.-%, preferably in the range of 0.25 to 3 wt.-%, more preferably in the range of 0.5 to 2 wt.-% based on the total weight of the compressed tablet.

Particularly suitable minerals according to the present invention are trace minerals such as manganese, zinc, iron, copper, iodine, selenium, and cobalt as well as macro minerals such as calcium, phosphorus and sodium. If present, the total amount of mineral(s) in the tablets according to the present invention is advantageously selected in the range of 0.01 to 30 wt.-%, preferably in the range of 0.05 to 20 wt.-%, most preferably in the range of 0.1 to 10 wt.-%.

Particularly suitable vitamins encompass fat-soluble vitamins such as vitamin A, vitamin D3, vitamin E, and vitamin K, e.g. vitamin K3 as well as water-soluble vitamins such as vitamin B12, biotin and choline, vitamin B1, vitamin B2, vitamin B6, niacin, folic acid and panthothenate, e.g. Ca-D-panthothenate. If present, the total amount of vitamin(s) in the tablets according to the present invention is advantageously selected in the range of 0.001 to 10 wt.-%, preferably in the range of 0.01 to 8 wt.-%, most preferably in the range of 0.1 to 5 wt.-%.

Particularly suitable proteins can be from vegetal or animal origin. The vegetable protein is selected from the group consisting of leguminous-based proteins, proteins from proteaginous plants and cereal based proteins, their crossbreds and mixtures thereof. The proteins from leguminous plants are selected from the group consisting of proteins from bean, soybean, pea, lupin, and alfalfa. The proteaginous plants are sunflower, rapeseed, linseed and peanut. Only the proteins of these proteaginous plants are of interest for the current invention. The cereal-based proteins are obtained from corn, wheat, rice, rye, oat, and sorghum. Preferably the vegetable protein is derived from wheat or corn, and mixtures thereof.

In a particular advantageous embodiment, the present invention relates to compressed tablets (IV) with all the preferences and definitions given herein, consisting essentially of
(i) 0.01 to 10 wt-%, preferably 0.05 to 5 wt.-%, more preferably 0.075 to 2.5 wt.-%, based on the total weight of the compressed tablet, of a compound of formula (I), optionally absorbed on a carrier and
(ii) at least 50 wt.-%, preferably at least 60 wt.-%, more preferably at least 70 wt.-%, based on the total weight of the compressed tablet, of gluten, preferably vital wheat gluten, and
(iii) 0 to 5 wt-%, preferably 0.25 to 3 wt.-%, more preferably 0.5 to 2 wt.-%, based on the total weight of the compressed tablet, of a lubricant, wherein preferably the lubricant is selected from calcium stearate and magnesium stearate, and
(iv) 0 to 25 wt.-%, preferably 0 to 20 wt.-%, more preferably from 0 to 10 wt.-%, based on the total weight of the compressed tablet, of at least one filler, wherein the filler is preferably selected from the group consisting of microcrystalline cellulose and limestone as well as mixtures thereof, and (iii) 0 to 10 wt-%, more preferably 0 to 8 wt.-%, most preferably 0 to 6 wt.-%, based on the total weight of the compressed tablet, of water.

The choice of the shape, volume and weight size of the compressed tablets according to the present invention will of course depend on the desired application. The shape of the compressed tablet can for example be sphere like, egg-like. The tablets of the present invention can be in the form of a pellet, a grain, a granule or any other type of particle, in so far it relates to compressed material.

Usually the tablets according to the present invention are several millimetres to several centimetres in size (such as 1 to 3 cm).

The weight of the tablet might vary according to the intended use and can e.g. range from 0.5 g to 2 g)

In a preferred embodiment, the compound of formula (I) is incorporated into the tablets according to the present invention adsorbed on a carrier, i.e. in the form of a powderous formulation. Said powderous formulation preferably consists essentially of a compound of formula (I), an edible oil and a carrier.

Suitable carriers to adsorb compounds of formula (I) encompass silica, maltodextrin, limestone, cyclodextrin, wheat as well as mixtures thereof. Particularly preferred in all embodiments is the use of silica (silicone dioxide) as carrier.

Suitable edible oils e.g. for diluting the compound of formula (I) before absorption on the carrier encompass propyleneglycol, corn oil, rapeseed oil, sunflower oil, middle chain triglyceride (MCT) and glycerol as well as mixtures thereof such as more in particular propyleneglycol.

The preparation of such powderous formulation is well known to a person skilled in the art. An exemplary preparation method includes dilution of the compound of formula (I) in the edible oil and spraying the resulting solution onto the carrier or admixed it with the carrier.

It is also possible that the compound of formula (I) is, optionally in the presence of an edible oil, diluted in an organic solvent suitable for the preparation of food or feed products such as e.g. dichloromethane, sprayed onto or admixed with the carrier followed by evaporation of the organic solvent.

In a particular advantageous embodiment, the powderous formulation comprising a compound of formula (I) consists essentially of silica, propyleneglycol and a compound of formula (I). More preferably, the powderous formulation consists essentially of 5-20 wt.-% of a compound of formula (I), 20 to 50 wt.-% of propyleneglycol and 30 to 60 wt.-% of silica, most preferably of 8-12 wt.-% of a compound of formula (I), 35 to 45 wt.-% of propyleneglycol and 45 to 55 wt.-% of silica.

Silica (also referred to as silicon dioxide) is a well-known carrier in the feed and food industry and refers to white microspheres of amorphous silica. Particular suitable silica according to the present invention is amorphous precipitated silica e.g. available as Ibersil D-250 at IQE Group, Sipernat 2200 at Evonik or Tixosil 68 at Solvay.

Preferably, the amount of the powderous formulation to be incorporated into the tablets according to the present invention is selected in the range of 1 to 30 wt.-%, preferably in the range of 5 to 20 wt.-%, most preferably in the range of 7 to 15 wt.-% such as in the range of 7 to 12 wt.-%, based on the compressed tablet.

In very specific embodiment, the present invention relates to compressed tablets (V) with all the preferences and definitions as given herein consisting essentially of (i) 5 to 20 wt.-%, preferably 7 to 12 wt.-%, based on the total weight of the compressed tablet, of a powderous formulation consisting essentially of 5-20 wt.-% of a compound of formula (I), 20 to 50 wt.-% of propyleneglycol and 30 to 60 wt.-% of silica, and (ii) at least 60 wt.-%, preferably at least 70 wt.-%, based on the total weight of the compressed tablet of vital wheat gluten, and (iii) 0.25 to 2 wt.-%, preferably 0.5 to 1.5 wt.-%, based on the total weight of the compressed tablet, of calcium stearate and/or magnesium stearate, and (iv) 0 to 25 wt.-%, preferably 0 to 20 wt.-%, more preferably from 0 to 10 wt.-% based on the total weight of the compressed tablet microcrystalline cellulose/or limestone, and (v) 0 to 8 wt.-%, most preferably 0 to 6 wt.-% based on the total weight of the compressed tablet, of water.

The term 'consisting essentially of' as used according to the present invention means that the total amount of the ingredients ideally adds up to 100 wt.-%. It is however not excluded that small amounts of impurities or additives may be present, with the proviso that the total amount of such impurities or additives is preferably less than 3 wt.-%, more preferably less than 2 wt.-%, most preferably less than 1 wt.-% and which are e.g. introduced via the respective raw materials.

The tablets according to the present invention can be produced according to standard methods in the art by compressing the admixed ingredients with a pressure of at least 5 KN to 100 kN.

Thus, the present invention also relates to a process for the production of compressed tablets according to the present invention, wherein a mixture consisting essentially of the compound of formula (I), the gluten and the optionally present additive(s) are compressed with a pressure of at least 5 KN, preferably in the range of 50 to 100 kN, more preferably in the range of 20 to 100 kN, most preferably in the range of 50 to 100 kN.

In a particular advantageous embodiment, the tablets according to the present invention are feed pellets, which are produced by a) feeding the compound of formula (I), the gluten and the optionally present additive(s) to a suitable equipment, b) providing into the equipment heated air or steam to increase the temperature and/or moisture content of the ingredient mixture pouring the heated ingredient mixture through a die for obtaining pellets c) drying and collecting the pellets.

In a preferred embodiment, the optionally present additives are selected from the group consisting of protein sources for feed purposes such as soy bean meal and/or rapeseed meal, phosphates, maize, yeast, trace minerals, salts and vitamins.

The compressed tablet according to the present invention can additionally be coated with customary coatings in the art such as wax or fats. If present, such coating is generally applied in amounts of 5 to 50 wt.-% based on the total weight of the tablet. Advantageously, the coating comprises at least one wax and/or at least one fat, which has a dropping point of from 30 to 85° C.

The dropping point of a material as used herein refers to the temperature (in ° C.) when the material begins to melt under standardized conditions. Thus, the material is heated so long until it changes the state of matter from solid to liquid. The dropping point is the temperature when the first dropping is released from the material. The determination of the dropping point (Tropfpunkt) is carried out as described in the standard norm DIN ISO 2176.

Particularly suitable waxes to be used as coating in the context of the present invention include organic compounds consisting of long alkyl chains, natural waxes (plant, animal) which are typically esters of fatty acids and long chain alcohols as well as synthetic waxes, which are long-chain hydrocarbons lacking functional groups.

Particularly suitable fats to be used as coating in the context of the present invention include a wide group of compounds which are soluble in organic solvents and largely insoluble in water such as hydrogenated fats (or saturated fats) which are generally triesters of glycerol and fatty acids. Suitable fats can have natural or synthetic origin. It is possible to hydrogenate a (poly)unsaturated fat to obtain a hydrogenated (saturated) fat.

Preferred examples of waxes and fats to be used as coating according to the present invention are glycerine monostearate, carnauba wax, candelilla wax, sugarcane wax, palmitic acid, stearic acid hydrogenated cottonseed oil, hydrogenated palm oil and hydrogenated rapeseed oil as well as mixtures thereof.

The tablets according to the present invention may be administered as such or may be admixed with customary feed compositions for ruminants.

As regards feed compositions for ruminants such as cows, as well as ingredients thereof, the ruminant diet is usually composed of an easily degradable fraction (named concentrate) and a fiber-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangels, fodder beet, and sugar beet (including sugar beet pulp and beet molasses) are used to feed ruminants. Still further crops are tubers such as potatoes, cassava and sweet potato. Silage is an ensiled version of the fiber-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage, concentrate, and tablets according to the present invention are mixed before serving.

The invention is illustrated by the following Examples. All temperatures are given in ° C. and all parts and percentages are related to the weight.

EXAMPLES

1a: Preparation of a Powderous Formulation (Form (I))

50 g of 20 wt.-% 3-nitrooxypropanol solution in propyleneglycol was added under gentle agitation to 50 g silica which was placed on a beaker at RT (±20° C.). After 5 minutes agitation, the adsorption is completed and a free-flowing powder is obtained. The powderous formulations are then allowed to stay at RT for another hour before use.

1b: Preparation of Tablets:

300 g powder mixture including Form (I) was prepared as outlined in table 2 by incorporating the listed ingredients step by step in a 1 L plastic container. The powder mix was mixed using a Bachofen Turbula mixer T2C for 10 min at 63 rpm then sieved through a 1.25 mm sieve then mixed again during 10 min at 63 rpm, then sieved again through a 1.25 mm sieve and finally mixed for another 10 min at 63 rpm. Following mixing as outlined above, the loose powder mixture was compressed using a tablet press Korsch XP1 to produce 1 g tablets using a compression force of 98 kN.

1c: Tablet Dispersion Properties

To test tablet disintegration properties one tablet as outlined in table 2 was added into 100 mL tap water. A visual observation was made initially and 24 hours. The results thereof are outlined in table 1 and FIGS. 1 to 4.

| Tablet | Visual appearance | | Rating | Figure |
|---|---|---|---|---|
| | initial | after 24 h | | |
| R2 | intact | cracked | Not OK | 1 |
| R3 | intact | cracked | Not OK | 2 |
| R4 | intact | cracked | Not OK | 3 |
| I1 | intact | intact | OK | 4 |

1d: Release Study:

The respective tablets were then placed in a beaker with 100 ml of demineralised water at room temperature. Each experiment was done in duplicate. After 5, 15, 30, 60, 90 minutes and 2, 6 and 24 hours 1 mL solution is taken out of the beaker and analysed for its 3-nitrooxypropanol content (HPLC). Time of 50% release is given in Table 2 (calculated by mathematical extrapolation of the obtained data points).

TABLE 2

| # | Ingredient | R1 | R2 | R3 | R4 | I1 | I2 | I3 | I4 | I5 | I6 | I7 | I8 |
|---|---|---|---|---|---|---|---|---|---|---|---|---|---|
| 1 | Form (I) | 10 | 10 | 10 | 10 | 10 | 10 | 10 | 10 | 10 | 10 | 10 | 10 |
| 2 | Microcrystalline cellulose | | 89 | | 25 | | 10 | 20 | 30 | | | | |
| 3 | Magnesium-stearate | | 1 | | | | | | | | | | |
| 4 | Calcium-stearate | | | | 1 | 1 | 1 | 1 | 1 | 1 | 1 | 1 | 1 |
| 5 | Monocalcium-phosphate | | | 21 | 21 | | | | | | | | |

TABLE 2-continued

| # | Ingredient | R1 | R2 | R3 | R4 | I1 | I2 | I3 | I4 | I5 | I6 | I7 | I8 |
|---|---|---|---|---|---|---|---|---|---|---|---|---|---|
| 6 | Limestone | | | 50 | 25 | | | | | 10 | 20 | 30 | 49 |
| 7 | Gluten | | | 18 | 18 | 89 | 79 | 69 | 59 | 79 | 69 | 59 | 40 |
| | Release after [h] | 0 | 0.2 | 0.5 | 0.75 | 7 | 6.5 | 4 | 2 | 6.5 | 4 | 2 | 2 |

1) Form prepared as outlined in example 1
2) Avicel PH102/FMC Biopolymer
3) Parteck LUB Mg-stearate/Merck
4) Calcium stearate/Riebel-de Haën
5) Monocalciumphosphate/Sigma-Aldrich
6) Avicarb/OMYA
7) Vitene ®/Roquette (Vital wheat Gluten)

As can be retrieved from table 2, the tablets according to the present invention show a significantly increased retention of the active.

The invention claimed is:

1. A compressed tablet comprising a compressed mixture of:
   (i) 1 to 30 wt. %, based on the total weight of the compressed tablet, of a powderous formulation comprising:
      (a) 45 to 55 wt. %, based on the total weight of the powderous formulation, of silica as a carrier,
      (b) 10 to 20 wt. %, based on the total weight of the powderous formulation, of 3-nitrooxypropanol as an active compound which is absorbed on the carrier, and
      (c) 35 to 45 wt. %, based on the total weight of the powderous formulation, of propylene glycol, and
   (ii) at least 69 wt. %, based on the total weight of the compressed tablet, of vital wheat gluten, wherein the tablet retains at least 50% of the active ingredient after 4 hours in water and remains intact in water after 24 hours in water.

2. The compressed tablet according to claim 1, further comprising at least one additive in an amount of 1 to 40 wt. %, based on the total weight of the compressed tablet.

3. The compressed tablet according to claim 2, wherein the at least one additive is selected from the group consisting of fillers, lubricants, proteins, dyes, flavours, sweeteners, minerals, vitamins and antioxidants.

4. The compressed tablet according to claim 1, wherein the compressed tablet further comprises a coating.

5. The compressed tablet according to claim 4, wherein the coating is selected from the group consisting of glycerine monostearate, carnauba wax, candelilla wax, sugarcane wax, palmitic acid, stearic acid, hydrogenated cottonseed oil, hydrogenated palm oil, hydrogenated rapeseed oil and mixtures thereof.

6. The compressed tablet according to claim 1, wherein the vital wheat gluten is present in an amount of at least 70 wt. %, based on the total weight of the compressed tablet.

7. The compressed tablet according to claim 1, wherein the active compound is present in an amount of 0.05 to 5 wt. %, based on the total weight of the compressed tablet.

8. The compressed tablet according to claim 1, wherein the active compound is present in an amount of 0.075 to 2.5 wt. %, based on the total weight of the compressed tablet.

9. The compressed tablet according to claim 1 further comprising at least one additive in an amount of 1 to 30 wt. %, based on the total weight of the compressed tablet.

10. The compressed tablet according to claim 1 further comprising at least one additive in an amount of 1 to 20 wt. %, based on the total weight of the compressed tablet.

11. A process for the preparation of the compressed tablet according to claim 1, wherein the process comprises the steps of: (a) forming a powderous formulation mixture by mixing (i) 1 to 30 wt. %, based on the total weight of the compressed tablet, of the powderous formulation and (ii) at least 69 wt. %, based on the total weight of the compressed tablet, of the vital wheat gluten, and thereafter (b) compressing the powderous formulation mixture at a pressure of at least 5 KN to thereby form the compressed tablet.

* * * * *